United States Patent
Flood

(10) Patent No.: US 10,071,972 B2
(45) Date of Patent: Sep. 11, 2018

(54) PROCESS FOR THE PREPARATION OF TRIAZINE CARBAMATES

(71) Applicant: ALLNEX IP S.à.r.l., Luxembourg (LU)

(72) Inventor: Lawrence Flood, Norwalk, CT (US)

(73) Assignee: ALLNEX NETHERLANDS B.V., Bergen op Zoom (NL)

( * ) Notice: Subject to any disclaimer, the term of this patent is extended or adjusted under 35 U.S.C. 154(b) by 0 days.

(21) Appl. No.: 15/505,337

(22) PCT Filed: Sep. 7, 2015

(86) PCT No.: PCT/EP2015/070369
§ 371 (c)(1),
(2) Date: Feb. 21, 2017

(87) PCT Pub. No.: WO2016/037973
PCT Pub. Date: Mar. 17, 2016

(65) Prior Publication Data
US 2017/0233353 A1     Aug. 17, 2017

(30) Foreign Application Priority Data
Sep. 9, 2014  (EP) .................................. 14184020

(51) Int. Cl.
*C07D 251/70* (2006.01)
*C07D 251/54* (2006.01)
*C07D 251/24* (2006.01)
*C07D 251/18* (2006.01)

(52) U.S. Cl.
CPC .......... *C07D 251/24* (2013.01); *C07D 251/18* (2013.01); *C07D 251/54* (2013.01); *C07D 251/70* (2013.01)

(58) Field of Classification Search
CPC .. C07D 251/18; C07D 251/48; C07D 251/50; C07D 251/70

USPC ....... 544/196, 200, 204, 205, 206, 207, 208, 544/209
See application file for complete search history.

(56) References Cited

U.S. PATENT DOCUMENTS

| | | | |
|---|---|---|---|
| 5,705,641 A | 1/1998 | Flood et al. | |
| 7,169,923 B2 * | 1/2007 | Schneider | C07D 251/70 544/196 |
| 7,507,818 B2 * | 3/2009 | Schneider | C07D 251/54 544/196 |
| 9,499,498 B2 * | 11/2016 | Jacobs, III | C07D 251/70 |
| 2006/0069254 A1 | 3/2006 | Schneider et al. | |
| 2007/0083047 A1 | 4/2007 | Schneider et al. | |

FOREIGN PATENT DOCUMENTS

| | | |
|---|---|---|
| WO | 03/035628 | 5/2003 |
| WO | 2004/054990 | 7/2004 |

OTHER PUBLICATIONS

International Search Report dated Oct. 14, 2015 in International Application No. PCT/EP2015/070369.

* cited by examiner

*Primary Examiner* — Venkataraman Balasubramanian
(74) *Attorney, Agent, or Firm* — Wenderoth, Lind & Ponack, L.L.P.

(57) ABSTRACT

This invention relates to a process for the preparation of triazine carbamates by reacting a mixture of an aminotriazine A having at least two amino groups per molecule, an organic carbonate C, and a base B selected from the group consisting of alkoxides, and arylalkoxides of metals M, which may be alkali or earth alkali metals, and a solvent S which is a monohydric alcohol solvent $R^2OH$ or a mixture of solvents that comprises a monohydric alcohol $R^2OH$, and a monohydric alcohol $R^3OH$, or a mixture of solvents that comprises a monohydric alcohol $R^2OH$ with a further solvent selected from the group consisting of ether, alcohol, and hydrocarbon solvents, and adding to the products of the said reaction, an acid or a solution of an acid in a solvent.

18 Claims, No Drawings

US 10,071,972 B2

PROCESS FOR THE PREPARATION OF TRIAZINE CARBAMATES

FIELD OF THE INVENTION

This invention relates to a process to prepare triazine carbamates by reacting in a solvent or in a solvent mixture, aminotriazines and organic carbonates in the presence of basic metal compounds.

BACKGROUND OF THE INVENTION

A process for the preparation of an at least bis-carbamate-functional triazine has been known from U.S. Pat. No. 5,705,641. An "at least bis-carbamate-functional triazine" is a 1,3,5-triazine having at least two functional groups which are carbamate groups. This process involves reacting an amino-functional 1,3,5-triazine having at least two amino groups with an acyclic organic carbonate, in the presence of a base. Useful bases as mentioned in this patent are alkali metal hydrides, alkali metal alkoxides, alkali metal hydroxides, alkali metal oxides, alkali metal carbonates, quaternary ammonium alkoxides, quaternary ammonium hydroxides, quaternary phosphonium alkoxides, quaternary phosphonium hydroxides, tertiary amines, and mixtures thereof. Sodium and potassium alkoxides are most preferred, and include linear, branched and cyclic alkyl group containing alkoxides and mixtures thereof. The reaction may be carried out in a solvent; as useful solvents, alcohol, ether, hydrocarbon, and amide solvents, such as N,N-dialkylformamide, are mentioned; alcohol solvents are preferred and include methanol, ethanol, propanol, butanol, pentanol, and hexanol; and also diols, viz., ethylene glycol, 1,2- and 1,3-propylene glycol, 1,4- and 2,3-butylene glycol, and isomers or mixtures of these. In the examples, n-butanol, methanol, N,N-dimethyl formamide, ethanol, sec.-butyl alcohol, isopropyl alcohol, and 2-ethylhexyl alcohol are used.

It has been found in the experiments on which the present invention is based that excessively high viscosity occurs during the reaction which leads to excessive energy consumption for homogenisation during the reaction, and either the need to use special equipment such as thin film reactors or kneaders, or the need to the use of more diluted reaction mixtures with the consequent loss in space-time yield. It has therefore been desired to reduce the viscosity of the reaction mixture without having to resort to lower concentrations, or having to use special equipment. Reduced viscosity, in other words, enhanced flowability and hence, easier transferability of the reaction mixture allows to increase the concentration of the reactants while maintaining a viscosity which allows simple handling of the reaction mixture, and thus also to increase the concentration of the desired reaction product in the reaction product mixture, thereby increasing the space-time yield for the reaction.

Additionally, this increased flowability allows more efficient neutralisation due to easier and faster mixing in a wider temperature range.

SUMMARY OF THE INVENTION

It has been discovered in the experiments on which the present invention is based that the viscosity of the reaction mixture can be reduced by the following measures:
a base B is used which is an alkoxide $M(OR^1)_a$ of a metal M which is selected from the group consisting of alkali metals (a=1) and earth alkali metals (a=2), or mixtures thereof with a further alkoxide $M(OR^0)_a$, where $R^0$ and $R^1$ are different from each other, together with a solvent that is selected from the group consisting of aliphatic hydrocarbon solvents, aromatic hydrocarbon solvents, mixed aliphatic-aromatic hydrocarbon solvents, aliphatic glycols, monoalkyl ethers of aliphatic glycols, dialkyl ethers of aliphatic glycols, and linear, branched or cyclic aliphatic ethers, or
a monohydric alcohol solvent $R^2OH$, or
a mixture of solvents that comprises a mass fraction of at least 2% of a monohydric alcohol $R^2OH$ with a further solvent that
is a monohydric alcohol $R^3OH$ wherein $R^2$ and $R^3$ are different from each other, or
is selected from the group consisting of aliphatic hydrocarbon solvents, aromatic hydrocarbon solvents, mixed aliphatic-aromatic hydrocarbon solvents, aliphatic glycols, monoalkyl ethers of aliphatic glycols, dialkyl ethers of aliphatic glycols, and linear, branched or cyclic aliphatic ethers,
wherein there is at least one alkyl group $R^i$ selected from the group consisting of $R^0$, $R^1$, $R^2$, and $R^3$ (i being one of 0, 1, 2, and 3) for which the following relations are true:
$R^i \neq R^j$ for all j selected from the group consisting of 0, 1, 2, and 3 with the condition that i≠j, and $$n(R^i) \geq [n(R^0)+n(R^1)+n(R^2)+n(R^3)] \cdot 0.02,$$

for all values of i individually, where n(R) is the amount of substance, with the SI unit "mol", of an alkyl group $R^i$ which stands for any of $R^0$, $R^1$, $R^2$, and $R^3$. In other words, the amount of substance fraction $x(R^i)=n(R^i)/[n(R^0)+n(R^1)+n(R^2)+n(R^3)]$ of each of the alkyl groups $R^0$, $R^1$, $R^2$, and $R^3$ in the reaction mixture, i being any one of 0, 1, 2, and 3, is at least 0.02 mol/mol, or 2%, for all values of i.

Preferably, the alkyl group $R^1$ is a tertiary alkyl group. Particularly high reduction in viscosity has been realised if $R^1$ is a tertiary alkyl group selected from the group consisting of a tert.-butyl, —C(CH$_3$)$_3$ group and a tert.-pentyl, (CH$_3$)$_2$C—CH$_2$—CH$_3$ group. It has been shown to be advantageous to use a monohydric alcohol $R^2OH$ as solvent which has a linear alkyl group $R^2$ in combination with an alkoxide having a tertiary alkyl group $R^1$. Hereinafter, the tert.-pentyl group is written as "—C(CH$_3$)$_2$—CH$_2$—CH$_3$" where it is understood that there is one tertiary carbon atom that has two methyl substituents and one ethyl substituent.

An even higher reduction in viscosity has been realised if a mixture of monohydric alcohol solvents $R^2OH$ and $R^3OH$ where $R^2$ and $R^3$ are different from each other, is used in conjunction with a mixture of metal alkoxides $M(OR^1)_a$ and $M(OR^0)_a$ where $R^1$ is a tertiary alkyl group such as tert.-butyl or tert.-pentyl, and where $R^3$ is also a tertiary alkyl group such as tert.-butyl or tert.-pentyl.

It is also possible to use, instead of the alkoxide $M(OR^1)_a$, an arylalkoxide $M(OR^6)_a$ of a metal M which may be an alkali metal (a=1) or an earth alkali metal (a=2), where $R^6$ is an aryl-alkylene residue of formula Ar-Alk- where Ar— is an aryl group having from five to fourteen carbon atoms, and -Alk- is an alkane diyl group having from one to twelve carbon atoms, with an alcohol, ether or hydrocarbon solvent.

The invention relates therefore to a process for the preparation of triazine carbamates by reacting a mixture of
an amino-1,3,5-triazine A having at least two amino groups per molecule,
an organic carbonate C, and a base B selected from the group consisting of alkoxides, and arylalkoxides of metals M, which may be alkali or earth alkali metals, and if the base B is an alkoxide $M(OR^1)_a$ of a metal M which is selected from the group consisting of alkali metals (a=1) and earth alkali metals (a=2), or mixtures thereof with a further alkoxide $M(OR^0)_a$, where $R^0$ and $R^1$ are different from each other, a solvent S which is a monohydric alcohol solvent $R^2OH$ or a mixture of solvents that comprises a mass fraction of at least 2% of a monohydric alcohol $R^2OH$, and a monohydric alcohol solvent $R^3OH$, or a mixture of solvents that comprises a mass fraction of at least 2% of a monohydric alcohol $R^2OH$ with a further solvent selected from the group consisting of ether and hydrocarbon solvents, or a mixture of solvents that comprises a mass fraction of at least 2% of a monohydric alcohol $R^3OH$ with a further solvent selected from the group consisting of ether and hydrocarbon solvents, wherein $R^0$ and $R^1$ and $R^2$ and $R^3$ are each independently selected from the group consisting of alkyl groups having from one to twenty carbon atoms and each may be linear, branched or cyclic, and wherein there is at least one alkyl group $R^i$ selected from the group consisting of $R^0$, $R^1$, $R^2$, and $R^3$ wherein i is one of 0, 1, 2, and 3, for which the following relations are true: $R^i \neq R^j$ for all j selected from the group consisting of 0, 1, 2, and 3 with the condition that $i \neq j$, and $$n(R^i) \geq [n(R^0)+n(R^1)+n(R^2)+n(R^3)] \cdot 0.02,$$

where n(R) is the amount of substance, with the SI unit "mol", of an alkyl group R which stands for any of $R^0$, $R^1$, $R^2$, and $R^3$, or, if the base is an arylalkoxide $M(OR^6)_a$ of a metal M which is selected from the group consisting of alkali metals (a=1) and earth alkali metals (a=2), where $R^6$ is an aryl-alkylene residue of formula Ar-Alk- where Ar— is an aryl group having from five to fourteen carbon atoms, and -Alk- is an alkane diyl group having from one to twelve carbon atoms, preferably selected from the group consisting of Ph-CH$_2$—, Ph-CH$_2$—CH$_2$—, where Ph is a residue derived from benzene by removal of one hydrogen atom, or from a substituted benzene having one or more methoxy, ethoxy, methyl, ethyl, propyl, or isopropyl groups as substituents, a solvent S comprising a mixture of a monohydric alcohol solvent $R^2OH$, with a further solvent which may be selected from the group consisting of a monohydric alcohol solvent $R^3OH$, where $R^3$ is different from $R^2$, each being selected from the group consisting of alkyl groups having from one to twenty carbon atoms and each may be linear, branched or cyclic, a multifunctional alcohol solvent where the alcohol has two or more hydroxyl groups per molecule, and from two to twelve carbon atoms, and ether, and hydrocarbon solvents.

Preferably, at least one of the alkyl groups $R^1$ and $R^2$, and $R^3$ if present, and $R^0$ if present, is a tertiary alkyl group. Particularly high reduction in viscosity has been realised if $R^1$ is a tertiary alkyl group, such as a tert.-butyl, —C(CH$_3$)$_3$ group or a tert.-pentyl, —C(CH$_3$)$_2$—CH$_2$—CH$_3$ group. It has been shown to be advantageous to use a monohydric alcohol $R^2OH$ as solvent which has a linear alkyl group $R^2$ in combination with an alkoxide having a tertiary alkyl group $R^1$. It is further preferred to use a metal alkoxide $M(OR^1)_a$ as base wherein $R^1$ is a tertiary alkyl group, such as a tert.-butyl, —C(CH$_3$)$_3$ group or a tert.-pentyl, —C(CH$_3$)$_2$—CH$_2$—CH$_3$ group.

It is also preferred that $R^3$ is a tertiary alkyl group, such as a tert.-butyl, —C(CH$_3$)$_3$ group or a tert.-pentyl, —C(CH$_3$)$_2$—CH$_2$—CH$_3$ group. It is particularly preferred that both $R^1$ and $R^3$ are tertiary alkyl groups, which may be the same or may be different from each other, such as a tert.-butyl, —C(CH$_3$)$_3$ group or a tert.-pentyl, —C(CH$_3$)$_2$—CH$_2$—CH$_3$ group.

Particularly preferably, a mixture of monohydric alcohol solvents $R^2OH$ and $R^3OH$ is used as solvent S where $R^2$ and $R^3$ are different from each other, is used in conjunction with a mixture of metal alkoxides $M(OR^1)_a$ and $M(OR^0)_a$ where $R^1$ and $R^3$ are a tertiary alkyl groups which may be the same or may be different from each other, such as tert.-butyl or tert.-pentyl.

DETAILED DESCRIPTION OF THE PREFERRED EMBODIMENTS

The process of this invention may be conducted at a temperature of from −40° C. up to 150° C., preferably from 20° C. to 120° C. It is possible to charge first the amino-1,3,5-triazine component, A, and then adding concurrently or sequentially, the base B, and the organic carbonate C. It is also possible to charge a mixture of aminotriazine A, and organic carbonate C, and then adding the base B to initiate the reaction. The solvent S may be charged into the reaction vessel before any of the other components, or together with any one or more of the components. The preferred way is to initially charge the base B, preferably in the solvent S, and then to add jointly or consecutively, the aminotriazine A and the organic carbonate C.

The reaction may be conducted, in a preferred embodiment, with a stoichiometric excess of the organic carbonate C over the aminotriazine A, which organic carbonate C may serve as solvent or diluent, and where the excess of carbonate C is removed after completion of the reaction, and neutralisation of the base B, preferably by distillation of the excess organic carbonate C.

The aminotriazine A has at least two primary amino groups, and may be selected from the group consisting of melamine, formoguanamine, acetoguanamine, benzoguanamine and caprinoguanamine, and from an N-alkylmelamine, and an N,N-dialkylmelamine, in which the alkyl groups may be the same or may be different, and the alkyl groups may individually have from one to twenty carbon atoms, and may be linear, or branched if the number of carbon atoms is three or more, or cyclic if the number of carbon atoms is three or more. Particularly preferred are melamine, acetoguanamine, and benzoguanamine.

Preferred anions of the base B are alkoxides —OR$^1$. Particularly preferred are lithium alkoxides, sodium alkoxides, potassium alkoxides, and magnesium alkoxides, and mixtures of any of these. Especially preferred are lithium alkoxides, sodium alkoxides, and potassium alkoxides, and mixtures of any of these. Particularly preferred, the alkoxides are tertiary alkoxides, or a mixture of alkoxides comprising an amount of substance-fraction of at least 2% (0.02 mol/mol or 2 cmol/mol), preferably at least 5 cmol/mol, and more preferred, at least 10 cmol/mol, of tertiary alkoxides.

In a preferred embodiment, one or more of the methylene —CR$_2$— groups in the alkyl group $R^1$ may be replaced by an oxygen atom in the form of an ether bond, —O—. In this case, there is at least one, preferably at least two successive, carbon atoms between any two oxygen atoms in the alkyl chain, and at the end of the alkyl chain, such as —$CR^a_2$—O—[$CR^b_2$]$_n$—O—$CR^c_2$— and —$CR^d_2$—O—[$CR^e_2$]$_m$—, where n and m are at least 1, preferably at least 2, and R, $R^a$, $R^b$, $R^c$, $R^d$, and $R^e$ are each the same, or are different from each other, and stand for hydrogen —H, or an alkyl having from one to six carbon atoms. Such alkyl groups $R^1$ may preferably be derived from monoalkyl ethers of ethylene glycol or propylene glycol, and of their oligomers. Particularly preferred alkoxides in this embodiment are the methoxy ethoxides of alkali or earth alkali metals M, ($CH_3$—O—$CH_2$—$CH_2$—O—)$_a$M, and alkoxides derived from oligomeric ethylene glycol monoalkyl ethers [$C_pH_{2p+1}$—(O—$CH_2$—$CH_2$—)$_q$—O—]$_a$M, where p is an integer number of preferably from 1 to 6, q is an integer number of preferably from 2 to 10, and a and M are as defined supra.

In this case of alkoxide bases M($OR^1$)$_a$ of alkali (a=1) or earth alkali (a=2) metals, a solvent S is used which is
a monohydric alcohol solvent $R^2$OH or
a mixture of solvents that comprises a monohydric alcohol $R^2$OH, and a mass fraction of at least 2% of a monohydric alcohol $R^3$OH, wherein $R^3$ and are $R^2$ are different from each other and wherein $R^3$ preferably is a tertiary alkyl group such as tert.-butyl or tert.-pentyl, or
a mixture of solvents that comprises a monohydric alcohol $R^2$OH with a mass fraction of at least 2% of a further solvent selected from the group consisting of alcohols having more than one hydroxyl groups per molecule, ether and hydrocarbon solvents.

In the case of mixtures of alkoxides with different alkyl groups, the amount-of-substance ratio) n($R^1$)/n($R^0$) in the reaction mixture of the amount of substance n($R^1$) of alkoxy groups $R^1$O— to the amount of substance n($R^0$) of alkoxy groups $R^0$O— is preferably from 98 mol/2 mol to 2 mol/98 mol; particularly preferably from 95 mol/5 mol to 5 mol/95 mol. Lowest viscosities have been observed in a range of from 70 mol/30 mol to 30 mol/70 mol.

In the case of the base B being an arylalkoxide of a metal M which is selected from the group consisting of alkali metals and earth alkali metals, a solvent S is used comprising a mixture of a monohydric alcohol solvent $R^2$OH, with a further solvent which may be selected from the group consisting of a monohydric alcohol solvent $R^3$OH, where $R^3$ is different from $R^2$, and $R^3$ is a tertiary alkyl group such as tert.-butyl or tert.-pentyl, of a multifunctional alcohol solvent where the alcohol has two or more hydroxyl groups per molecule, and of ether and hydrocarbon solvents as detailed supra.

The alkyl groups $R^0$, $R^1$, $R^2$ and $R^3$ are independently of each other selected from alkyl groups derived from an alkane that may be linear, branched, or cyclic, by removal of one hydrogen atom, and having from one to twenty carbon atoms.

The preferred anions are alkoxides —$OR^1$ based on tertiary alcohols by removal of the hydrogen atom from the hydroxyl group, such as tert.-butoxide, and the alkoxides derived from 2-methyl-2-hydroxybutane, 3-methyl-3-hydroxypentane, and 3-ethyl-3-hydroxy-pentane. A tertiary alcohol, in agreement with the common organic nomenclature, has a hydroxyl group bound to a tertiary carbon atom.

The preferred alkyl groups $R^2$ of the alcohols $R^2$OH have from one to twenty carbon atoms and are linear or branched in a way that they have at least one carbon atom that is bound to three other carbon atoms, but have the free valence in a secondary or primary carbon atom, i. e. a carbon atom that is bound to two other carbon atoms, or to one other carbon atom, but not in a tertiary carbon atom. Particularly preferred as alcohols $R^2$OH are ethanol, n-propanol, isopropanol, n-butanol, iso-butanol, sec.-butanol, neopentanol, n-hexanol, n-octanol, 2-ethyl-hexanol, and mixtures of these. $R^1$ and $R^2$ are preferably different from each other.

The preferred alkyl groups $R^3$ of the alcohols $R^3$OH have from four to twenty carbon atoms and are branched in a way that they have at least one carbon atom that is bound to three other carbon atoms, and have the free valence in a tertiary, a secondary or primary carbon atom, i. e. a carbon atom that is bound to three other carbon atoms, or to two other carbon atoms, or to one other carbon atom. Particularly preferred as alcohols $R^3$OH are tert.-butanol, tert.-pentyl alcohol (=2-methyl-2-butanol), 2-methyl-2-pentanol, and 3-methyl-3-pentanol. $R^3$ and $R^2$ are preferably different from each other.

The most preferred embodiment comprises, as alcohol solvent, a mixture of n-butanol and tert.-butanol.

In the case where solvent mixtures are used, in addition to the minimum mass fraction recited for a component, as 2%, preferred mass fractions are, in each case, at least 5%, and particularly preferred, in each case, at least 10%, and with special preference, in each case, at least 20%, of this component.

A preferred embodiment comprises an in-situ synthesis of the metal alkoxides from corresponding metals or metal compounds, the metal preferably being an alkali metal or an earth alkali metal, and the metal compounds preferably being compounds of an alkali metal or compounds of an earth alkali metal, by reacting, preferably under heating, the metal(s) or metal compound(s), and an alcohol having from one to six carbon atoms, optionally in the presence of an entrainment agent, wherein the metal compounds are individually selected from the group consisting of metal hydrides, metal oxides, metal hydroxides, metal amides, metal alkoxides, and organometal compounds. It is preferred, also in this context, that the metals or metal compounds are at least two metals or metal compounds selected from the group consisting of alkali metals and earth alkali metals, and their compounds. Preferably, the entrainment agent which is optionally used is an alkane having at least six carbon atoms, or an aromatic or alkylaromatic compound such as toluene or xylene. In a further preferred embodiment, the in-situ formation of alkoxides may be done in the same vessel where the reaction between the mixture B of bases, the aminotriazine A, and the organic carbonate C is to be conducted.

The organic carbonate C has the structure $R^4$O—CO—$OR^5$, where $R^4$ and $R^5$ may be the same or may be different, and are individually selected from the group consisting of alkyl radicals having from one to twenty carbon atoms, and may be linear, or branched (if the number of carbon atoms is three or more) or cyclic (if the number of carbon atoms is three or more), or may together form an alkanediyl group having from two to twenty carbon atoms, which may be linear or branched (if the number of carbon atoms is three or more) or cyclic (if the number of carbon atoms is three or more). Preferred are dimethyl carbonate, diethyl carbonate, di-n-propyl carbonate, di-isopropyl carbonate, di-n-butyl carbonate, di-sec.-butyl carbonate, di-isobutyl carbonate, di-tert.-butyl carbonate and mixtures thereof. It is also possible to use cyclic carbonates such as ethylene carbonate, 1,2-propylene carbonate, and 1,3-propylene carbonate, or their mixtures, or also mixtures of cyclic carbonates and carbonates of formula $R^4$O—CO—$OR^5$ supra.

The hydrocarbon solvents may be selected from aliphatic, aromatic and from mixed aliphatic-aromatic hydrocarbon solvents having a boiling temperature at normal atmospheric pressure (0.1013 MPa) of at least 80° C. such as toluene, ethylbenzene, o-xylene, m-xylene, p-xylene, an isomer mixture of xylenes, mixtures of aromatic solvents such as those commercially available as ®Shellsol, Solvesso™, mixtures or aliphatic branched paraffins such as those commercially available as ®Shellsol T, ®Shellsol TD and ®Shellsol TC.

Alcohol solvents are preferably aliphatic alcohols having from four to twenty carbon atoms, such as hexanol, octanol, decanol, and dodecanol, aliphatic glycols having preferably from two to ten carbon atoms, such as ethylene glycol, 1,2-propylene glycol, 1,4-butylene glycol, and 1,6-hexandiol, as well as hydroxyl-functional ethers which are partial ethers of multi-functional alcohols having more than one hydroxyl group and preferably from two to ten carbon atoms and alkanols having preferably from one to five carbon atoms, such as ethylene glycol monomethyl ether, and diethylene glycol monobutyl ether, aliphatic ethers which may be linear, branched or cyclic and may have from four to thirty carbon atoms, such as tetrahydrofuran, diethylene glycol diethyl ether, triethylene glycol dimethyl ether, and 1,4-dioxane.

It is also possible, in a less preferred embodiment, to use esters which are not easily hydrolysed, such as esters from branched acids, and of branched alcohols whereof the functional group is on a sterically hindered carbon atom such as a tertiary carbon atom, like tert.-butyl acetate.

Avoidance of high viscosity reaction intermediates that are encountered with the base and carbonate processes known from the patent literature allows the use of much higher reaction concentrations and thus significant improvements in product throughput and space-time-yield. The process of this invention also allows to utilise conventional reactor designs with conventional stirrer configurations, while in the processes known from the patent literature, large amounts of solvents are needed to prevent clogging and adhesion of the reaction mass to the stirrer in a conventional reactor set-up. While in the base carbonate processes used heretofore, the encountered high intermediate reaction viscosities dictated that the product concentrations (mass fraction of triazine carbamate in the reaction mixture after completion of the reaction) could be no higher than from 10% to 15% in order for the reaction mixture to be fluid enough for stirring, the process of this invention allows to increase reaction product concentrations such as by a factor of 1.5 or more compared to a process using a single alkali alkoxide base in combination with an a alcohol derived from the same alkyl group such as sodium n-butoxide combined with n-butanol as a solvent, or potassium n-butoxide combined with n-butanol as a solvent, while maintaining efficient stirring.

After completion of the reaction, the reaction mixture is usually cooled and neutralised by addition of acid, or by addition of the reaction mixture to an acid, to obtain the triazine carbamate reaction product, and to convert the base to the corresponding salts, and, e. g., regeneration of the alcohol in the case of using alkoxides as the base. The acid is used as such, or is dissolved in a solvent S' selected from the group consisting of water, alcohols, ethers, and hydrocarbon solvents, where S' is preferably an alcohol selected from the same groups as $R^2OH$ and $R^3OH$, and is the same, or is different therefrom, or water. In the case of inorganic acids such as nitric acid, or sulphuric acid, dilution with water is preferred. As is obvious, the lower the neutralisation temperature, the higher will be the viscosity, ceteris paribus. It has been found in the experiments underlying the present invention that a higher neutralisation temperature leads to an increase in the amount of bis-carbamate found as product, in the mixture of mono-, bis-, and tris-carbamate in the case of reacting a triaminotriazine such as melamine. For optimum crosslinking property of the melamine-derived alkoxy-carbonylaminotriazine, a mass fraction of bis-carbamate in excess of 10% (and accordingly, a mass fraction of mono-carbamate of more than 1%) in the mixture of mono-, bis-, and tris-carbamate should be avoided. Therefore, lower neutralisation temperatures are favoured even though this necessitates lower concentrations (more solvent) in the reaction mixture to keep the mixture at sufficiently low viscosity.

On the other hand, early neutralisation (i. e. immediately after completion of the reaction) saves time in the total process, and is therefore advantageous. It has been found, surprisingly, that the use of an alkoxide base with a tertiary alkyl group in combination with an alcohol derived from a linear alkyl group results in a lower mass fraction of bis-carbamate in the product mixture than in the case of using a system where an alcohol is used as solvent which corresponds to the alkoxy group of the alkoxide base (i. e. both having the same alkyl group). This effect is particularly marked when using an alkali tertiary butoxide as base, and n-butanol as solvent or when using an alkali n-alkoxide as base in conjunction with alkali tert.-alkoxide as co-base with n-butanol as solvent with tert-butanol as co-solvent. Using such combination is therefore a particularly preferred embodiment, especially preferred in combination with a base comprising at least two different metal alkoxides.

In the neutralisation step, the preferred acids are inorganic acids such as sulphuric, nitric or phosphoric acid, as well as the stronger organic acids, particularly the lower aliphatic acids such as formic and acetic acid. It is further preferred to dilute these acids with water, or with a solvent S' which is an alcohol having one or more hydroxyl groups per molecule, preferably an aliphatic alcohol that had been used in the reaction between the aminotriazine and the organic carbonate. Oxydising acids such as nitric acid should always be used in aqueously diluted form.

The triazine carbamates that are prepared by the process of this invention can be used to form crosslinked coatings, inks, adhesives, sealants, composites, laminates, sizings for textiles and carbon fibers, binders for paper and particle board, as well as numerous other thermosetting applications when heated with suitable polymeric or oligomeric backbone materials for a sufficient time and temperature to effect cure. The suitable polymeric or oligomeric backbone materials have the appropriate reactivity and functional groups to react with said triazine carbamate crosslinker composition with or without a catalyst, to form a crosslinked network after curing. Particularly preferred are those polymeric or oligomeric backbone materials having hydroxyl, or carboxyl, or amino functional groups, or combinations thereof. The resulting composition can be applied to the substrate in the typical manner such as spraying, dipping, roller coating, brushing, etc. These compositions are particularly suitable for durable, light stable coatings useful for automotive topcoats and other UV stable outdoor applications requiring high durability.

The invention is further explained in the following examples which are not to be construed as limiting.

The following expressions are used in the examples, and also in the specification, with the meanings as defined herein:

"Strength" or "concentration" stands for a mass fraction, particularly used in aqueously diluted acids or bases, where, e.g. "50% strength sulfuric acid" refers to an aqueous dilution of sulfuric acid with a mass fraction of 50% of $H_2SO_4$ in the diluted acid.

Brookfield viscosity was measured in a Brookfield DV-II+ rotational viscometer (Brookfield Engineering Laboratories Inc., Middleboro Mass.) with a SC4-27 spindle and a Thermosel heated measuring chamber which allows the use of small samples (not more than 11 g) and exact temperature control up to 300° C. Samples were taken from the reaction mixture at the end of the 90° C. hold period of the examples, and placed in a pre-heated measuring chamber, which was then loaded into the heating unit which had been pre-heated to 90° C. and the SC4-27 spindle lowered into the reaction medium. The temperature of the slurry was then allowed to drop in predefined stages, and viscosity was measured at 0.5 min$^{-1}$ (0.5 rpm) until the viscosity reading went off scale, at a value of more than 500 Pa·s (500 000 cP, "centipoise").

COMPARATIVE EXAMPLE 1

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for dry nitrogen were added over an hour with stirring in the following order: 240 g solution of sodium n-butoxide in n-butanol having a mass fraction of solids of 21%, 15.8 g of melamine and 36.0 g of dimethylcarbonate with a dry nitrogen sparge. The total mass fraction of the reaction solids after all reagent additions was approx. 14%. Under continued stirring the resulting white slurry was then heated to 90° C. Within thirty minutes at 90° C., the reaction mixture became extremely viscous and paste-like. The thick reaction slurry was held at 90° C. for an additional hour whereafter a 11.0 g sample was removed for Brookfield viscosity measurement with the results of 340 Pa·s at 90° C., with a speed of rotation of 0.5 min$^{-1}$, and 500 Pa·s at 80° C. and the same speed of rotation. The reaction mixture was then cooled to from 15° C. to 20° C. To a second reactor ("reactor 2"), with good stirring, 23.4 g of concentrated sulfuric acid (mass fraction of H$_2$SO$_4$ of 96%) were slowly added to 37 g of deaerated n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 below 20° C. during the addition. After addition of butanolic sulfuric acid was complete, the final pH of the reaction mixture (measured as supra on a dilution of 3 g of reaction mixture sample in 3 g of water) was adjusted to a pH value of approximately 5.5, if necessary, with further solution of concentrated sulfuric acid in n-butanol. The reaction mixture was then filtered free of salts and the solution of product was then analysed by HPLC and $^{13}$C NMR and shown to be composed of 97% of 2,4,6-tris-n-butyl- and 2,4,6-tris-methyl- and mixed 2,4,6-tris-n-butyl-methyl-carbamoyl-1,3,5-triazines with 3% of the bis-n-butyl- and bis-n-methyl- and mixed n-butyl-methyl-carbamoyl-1,3,5-triazine including traces of mono-n-butyl-carbamoyl-1,3,5-triazine and mono-methylcarbamoyl-1,3,5-triazine.

COMPARATIVE EXAMPLE 2

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for dry nitrogen were added over an hour with stirring in the following order: 240 g of a solution of sodium n-butoxide in n-butanol having a mass fraction of solids of 21%, 15.8 g of melamine and 36.0 g of dimethylcarbonate with a dry nitrogen sparge. The total mass fraction of the reaction solids after all reagent additions was approximately 14%. Under continued stirring the resulting white slurry was then heated to 90° C. Within thirty minutes at 90° C., the reaction mixture became extremely viscous and paste-like. The thick reaction slurry was held at 90° C. for an additional hour whereafter a 11.0 g sample was removed for Brookfield viscosity measurement with the result of 340 Pa·s at 90° C., and 500 Pa·s at 80° C.

The reaction mixture was then cooled to 57° C. To a second reactor ("reactor 2"), with good stirring, 23.4 g of concentrated sulfuric acid (mass fraction of H$_2$SO$_4$ of 96%) were slowly added to 37 g of deaerated n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 below at approximately 65° C. during the addition. After the addition of butanolic sulfuric acid was complete, the final pH of the reaction mixture (measured as supra on a dilution of 3 g of reaction mixture sample in 3 g of water) was adjusted to a pH value of approximately 5.5, if necessary, with further solution of concentrated sulfuric acid in n-butanol. The reaction mixture was then filtered free of salts and the solution of product was then analysed by HPLC and $^{13}$C NMR and shown to be composed of a mass fraction of 84 of tris-substituted products (2,4,6-tris-n-butyl-carbamoyl-1,3,5-triazine, 2,4,6-tris-methyl-carbamoyl-1,3,5-triazine and mixed 2,4,6-tris-n-butyl-methyl-carbamoyl-1,3,5-triazines) with a mass fraction of 16% of bis-substituted products (bis-n-butyl-carbamoyl-1,3,5-triazine, bis-n-methyl-carbamoyl-1,3,5-triazine, and mixed n-butyl-methyl-carbamoyl-1,3,5-triazine) including traces of mono-n-butyl-carbamoyl-1,3,5-triazine and mono-methylcarbamoyl-1,3,5-triazine.

EXAMPLE 2

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for dry nitrogen were added over an hour with stirring in the following order: 240 g solution of sodium n-butoxide in n-butanol having a mass fraction of solids of 21%, 15.8 g of melamine and 36.0 g of dimethylcarbonate with a dry nitrogen sparge. The total mass fraction of the reaction solids after all reagent additions was approximately 14.5%. Under continued stirring the resulting white slurry was then heated to 90° C. Within thirty minutes at 90° C., the reaction mixture became extremely viscous and paste-like. The thick reaction slurry was held at 90° C. for an additional hour and then 37 g of tert.-butanol were added, the mixture was stirred for thirty minutes, and a 10.5 g sample was removed for measuring the Brookfield viscosity, yielding the following results: 39 Pa·s at 90° C., and 500 Pa·s at 43° C., and the reaction mixture was then cooled to approximately 26° C. To a second reactor ("reactor 2"), with good stirring, 29.6 g of concentrated sulfuric acid (mass fraction of H$_2$SO$_4$ of 96%) were slowly added to 49.1 g of n-butanol with good cooling (ice-water) such that the temperature did not exceed 13° C.

during solution preparation. After complete addition of the sulfuric acid to the n-butanol in reactor 2, the acidic butanol solution was then transferred slowly in portions to reactor 1 under good stirring and cooling, keeping the temperature in reactor 1 between 25° C. and 30° C. during the addition. After the addition of butanolic sulfuric acid was complete, the final pH of the reaction mixture (measured as supra on a dilution of 3 g of reaction mixture sample in 3 g of water) was adjusted to a pH value between 4.5 and 6.5, if necessary, with further solution of concentrated sulfuric acid in n-butanol prepared as supra. The reaction mixture was then filtered free of salts and the solution of product was then analysed by HPLC and $^{13}$C NMR and shown to be mostly 2,4,6-tris-n-butyl- and 2,4,6-tris-methyl- and mixed 2,4,6-tris-n-butyl-methylcarbamoyl-1,3,5-triazines with a small amount of the bis-n-butyl- and bis-n-methyl- and mixed n-butyl-methyl-carbamoyl-1,3,5-triazine including traces of mono-n-butyl-carbamoyl-1,3,5-triazine and mono-methyl-carb-amoyl-1,3,5-triazine. The mass recovery of the product was 98% of the calculated value.

EXAMPLE 3

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for a dry nitrogen were added over half an hour with stirring in the following order: 473 g of a solution of sodium n-butoxide and sodium tert.-butoxide in a mixture of mass fractions of 86% of n-butanol and 14% of tert.-butanol prepared from sodium metal by reaction thereof with this butanol mixture, having a mass fraction of solids of 18%, 26.9 g of melamine and 62 g of dimethylcarbonate with a dry nitrogen sparge. The total mass fraction of the reaction solids after all reagent additions was approximately 18.5%. Under continued stirring the resulting white slurry was then heated to 90° C. The moderately light reaction slurry was held at 90° C. for ninety-six minutes, and a 10.8 g sample of the reaction mixture was removed for Brookfield viscosity measurement to yield values of 9 Pa·s at 90° C., and of 500 Pa·s at 17° C., and the reaction mixture was then cooled to 27° C. To a second reactor ("reactor 2"), with good stirring, 42 g of concentrated sulfuric acid (mass fraction of $H_2SO_4$ of 96%) were slowly added to 69.7 g of n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 between 27° C. and 33° C. during the addition. After addition of butanolic sulfuric acid was complete, the final pH of the reaction mixture (measured as supra on a dilution of 3 g of reaction mixture sample in 3 g of water) was adjusted to a pH value of approximately 5.5 with further solution of concentrated sulfuric acid in n-butanol prepared as described supra. The reaction mixture was then filtered free of salts and the solution of product was then analysed by HPLC and $^{13}$C NMR and shown to be composed of mass fractions of 94% of 2,4,6-tris-n-butyl- and 2,4,6-tris-methyl- and mixed 2,4,6-tris-n-butyl-methylcarbamoyl-1,3,5-triazines with 6% of the bis-n-butyl- and bis-n-methyl- and mixed n-butyl-methyl-carbamoyl-1,3,5-triazine including traces of mono-n-butyl-carbamoyl-1,3,5-triazine and mono-methyl-carbamoyl-1,3,5-triazine. The mass recovery of the product was 90% of the calculated value.

EXAMPLE 4

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for a dry nitrogen were added over an hour with stirring in the following order: 600 g of anhydrous n-butanol, 76 g of sodium tert.-butoxide, 25 g of melamine and 57.5 g of dimethylcarbonate with a dry nitrogen sparge. The total mass fraction of the reaction solids after all reagent additions was approximately 14.5%. Under continued stirring the resulting white slurry was then heated to 90° C. The moderately viscous slurry was held at 90° C. for one hundred minutes, and a 10.9 g sample was removed for Brookfield viscosity measurement yielding a value of 7 Pa·s at 90° C., and 500 Pa·s at 21° C. whereafter the reaction mixture was cooled to 57° C. To a second reactor ("reactor 2"), with good stirring, 42 g of concentrated sulfuric acid (having a mass fraction of $H_2SO_4$ of 96%) were slowly added to 70 g of n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 between 20° C. and 25° C. during the addition. After addition of butanolic sulfuric acid was complete, the final pH of the reaction mixture (measured as supra on a dilution of 3 g of reaction mixture sample in 3 g of water) was adjusted to a pH value of approximately 5.5 with further solution of concentrated sulfuric acid in n-butanol prepared as described supra. The reaction mixture was then filtered free of salts and the solution of product was then analysed by HPLC and $^{13}$C NMR and shown to be composed of mass fractions of 90% of 2,4,6-tris-n-butyl- and 2,4,6-tris-methyl- and mixed 2,4, 6-tris-n-butyl-methylcarbamoyl-1,3,5-triazines with 10% of the bis-n-butyl- and bis-n-methyl- and mixed n-butyl-methyl-carbamoyl-1,3,5-triazine including traces of mono-n-butyl-carbamoyl-1,3,5-triazine and mono-methylcarbamoyl-1,3,5-triazine. The mass recovery of the product was 97% of the calculated value.

EXAMPLE 5

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for dry nitrogen were added over an hour with stirring in the following order: 444 g of anhydrous n-butanol, 96 g of sodium tert.-butoxide, 31.5 g of melamine and 72.5 g of dimethylcarbonate with a dry nitrogen sparge. The total mass fraction of the reaction solids after all reagent additions was approximately 24.5%. Under continued stirring the resulting white slurry was then heated to 90° C. The moderately viscous slurry was held at 90° C. for sixty minutes, an 11.0 g sample was removed for Brookfield viscosity measurement yielding values of 300 Pa·s at 90° C., and 500 Pa·s at 69° C., and the reaction mixture was then cooled to 18° C. To a second reactor ("reactor 2"), with good stirring, 46 g of concentrated sulfuric acid (mass fraction of $H_2SO_4$ of 96%) were slowly added to 76 g of n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 between 9° C. and 25° C. during the addition. After addition of butanolic sulfuric acid was complete, the final pH of the reaction mixture (measured as supra on a dilution of 3 g of reaction mixture sample in 3 g of water) was adjusted to a pH value of approximately 5.5 with further solution of concentrated sulfuric acid in n-butanol prepared as described supra. The reaction mixture was then filtered free of salts and the solution of product was then analysed by HPLC and $^{13}$C NMR and shown to be composed 90% of 2,4,6-tris-n-butyl- and 2,4,6-tris-methyl- and mixed 2,4,6-tris-n-butyl-methylcarbamoyl-1,3,5-triazines with 10% of the bis-n-butyl- and bis-n-methyl- and mixed n-butyl-methyl-carbamoyl-1,3,5-triazine including traces of mono-n-butyl-carbamoyl-1,3,5-triazine and mono-methyl-carbamoyl-1,3,5-triazine. The mass recovery of the product was 98% of the calculated value.

EXAMPLE 6

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for dry nitrogen were added over an hour with stirring in the following order: 555 g of anhydrous n-butanol, 73.5 g of sodium tert.-pentoxide, 20 g of melamine and 46 g of dimethylcarbonate with a dry nitrogen sparge. The total mass fraction of the reaction solids after all reagent additions was approximately 14.5%. Under continued stirring the resulting white slurry was then heated to 90° C. The light viscous slurry was held at 90° C. for one hundred and two minutes, a 10.6 g sample was removed for Brookfield viscosity measurement yielding values of 33 Pa·s at 90° C., and 500 Pa·s at 28° C., and the reaction mixture was then cooled to 26° C. To a second reactor ("reactor 2"), with good stirring, 33 g of concentrated sulfuric acid (mass fraction of $H_2SO_4$ of 96%) were slowly added to 55 g of n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 between 26° C. and 37° C. during the addition. After addition of butanolic sulfuric acid was complete, the final pH of the reaction mixture (measured as supra on a dilution of 3 g of reaction mixture sample in 3 g of water) was adjusted to a pH value of approximately 5.5, with further solution of anhydrous sulfuric acid in n-butanol prepared as described supra. The reaction mixture was then filtered free of salts and the solution of product was then analysed by HPLC and $^{13}$C NMR and shown to be composed of 96% of 2,4,6-tris-n-butyl- and 2,4,6-tris-methyl- and mixed 2,4,6-tris-n-butyl-methylcarbamoyl-1,3,5-triazines with 4% of the bis-n-butyl- and bis-n-methyl- and mixed n-butyl-methyl-carbamoyl-1,3,5-triazine including traces of mono-n-butyl-carbamoyl-1,3,5-triazine and mono-methylcarbamoyl-1,3,5-triazine. The mass recovery of the product was 98% of the calculated value.

EXAMPLE 7

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for a dry nitrogen atmosphere were added over an hour with stirring in the following order: 333 g of anhydrous n-butanol, 67 g of xylenes, 76 g of sodium tert.-butoxide, 25 g of melamine and 58 g of dimethylcarbonate with a dry nitrogen sparge. The total mass fraction of the reaction solids after all reagent additions was approximately 22.5%. Under continued stirring the resulting white slurry was then heated to 90° C. The moderately viscous slurry was held at 90° C. for eighty-eight minutes, an 11.3 g sample was removed for Brookfield viscosity measurement yielding values of 36 Pa·s at 90° C., and 500 Pa·s at less than 20° C., and the reaction mixture was then cooled to 36° C. To a second reactor ("reactor 2"), with good stirring, 40 g of concentrated sulfuric acid (mass fraction of $H_2SO_4$ of 96%) were slowly added to 66 g of n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 between 36° C. and 39° C. during the addition. After addition of butanolic sulfuric acid was complete, the final pH of the reaction mixture (measured as supra on a dilution of 3 g of reaction mixture sample in 3 g of water) was adjusted to a pH value of approximately 5.5, with further solution of anhydrous sulfuric acid in n-butanol prepared as described supra. The reaction mixture was then filtered free of salts and the solution of product was then analysed by HPLC and $^{13}$C NMR and shown to be composed of 93% of 2,4,6-tris-n-butyl- and 2,4,6-tris-methyl- and mixed 2,4,6-tris-n-butyl-methylcarbamoyl-1,3,5-triazines with 7% of the bis-n-butyl- and bis-n-methyl- and mixed n-butyl-methyl-carbamoyl-1,3,5-triazine including traces of mono-n-butyl-carbamoyl-1,3,5-triazine and mono-methylcarbamoyl-1,3,5-triazine. The mass recovery of the product was 96% of the calculated value.

EXAMPLE 8

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for a dry nitrogen were added over an hour with stirring in the following order: 207 g of a solution of sodium n-butoxide in n-butanol having a mass fraction of solids of 21%, 70 g of anhydrous n-butanol, 27.5 g of tert-butanol, 2.4 g of sodium tert-butoxide, 15 g of melamine and 34.5 g of dimethylcarbonate with a dry nitrogen sparge. The total mass fraction of the reaction solids after all reagent additions was approximately 14.5%. Under continued stirring the resulting white slurry was then heated to 90° C. The light viscous slurry was held at 90° C. for ninety-one minutes, an 11 g sample was removed for measuring the Brookfield viscosity yielding the following results: 32 Pa·s at 90° C., 500 Pa·s at 32° C., and the reaction mixture was then cooled to 33° C. To a second reactor ("reactor 2"), with good stirring, 24 g of concentrated sulfuric acid (mass fraction of $H_2SO_4$ of 96%) were slowly added to 39 g of n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 between 33° C. and 39° C. during the addition. After addition of butanolic sulfuric acid was complete, the final pH of the reaction mixture (measured as supra on a dilution of 3 g of reaction mixture sample in 3 g of water) was adjusted to a pH value between 4.5 and 6.5, if necessary, with further solution of anhydrous sulfuric acid in n-butanol. The reaction mixture was then filtered free of salts and the solution of product was then analysed by HPLC and $^{13}C$ NMR and shown to be composed of a mass fraction of 93% of the tris-substituted products (2,4,6-tris-n-butyl-carbamoyl-1,3,5-triazine and 2,4,6-tris-methyl-carbamoyl-1,3,5-triazine and mixed 2,4,6-tris-n-butyl-methylcarbamoyl-1,3,5-triazines), with 7% of the bis-substituted products (bis-n-butyl-carbamoyl-1,3,5-triazine, bis-n-methyl-carbamoyl-1,3,5-triazine, and mixed n-butyl-methyl-carbamoyl-1,3,5-triazine) including traces of mono-n-butyl-carbamoyl-1,3,5-triazine and mono-methyl-carbamoyl-1,3,5-triazine. The mass recovery of the product was 97% of the calculated value.

EXAMPLE 9

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for a dry nitrogen were added over an hour with stirring in the following order: 227 g of a solution of sodium n-butoxide in n-butanol having a mass fraction of solids of 21%, 30 g of tert.-butanol, 3 g of sodium tert.-butoxide, 16.5 g of melamine and 38 g of dimethylcarbonate with a dry nitrogen sparge. The total mass fraction of the reaction solids after all reagent additions was approximately 19.5%. Under continued stirring the resulting white slurry was then heated to 90° C. The light viscous slurry was held at 90° C. for one hundred and two minutes, a 10 g sample was removed for measuring the Brookfield viscosity yielding the following results: 111 Pa·s at 90° C., 500 Pa·s at 48° C., and the reaction mixture was then cooled to 33° C. To a second reactor ("reactor 2"), with good stirring, 25 g of concentrated sulfuric acid (mass fraction of $H_2SO_4$ of 96%) were slowly added to 42 g of n-butanol with good cooling (ice-water) such that the temperature did not exceed 13° C. during solution preparation. After complete addition of the sulfuric acid to the n-butanol in reactor 2, the acidic butanol solution was then transferred slowly in portions to reactor 1 under good stirring and cooling, keeping the temperature in reactor 1 between 33° C. and 39° C. during the addition. After the addition of the butanolic sulfuric acid was complete, the final pH of the reaction mixture (measured as supra on a dilution of 3 g of reaction mixture sample in 3 g of water) was adjusted to a pH value between 4.5 and 6.5, if necessary, with further solution of anhydrous sulfuric acid in n-butanol. The reaction mixture was then filtered free of salts and the solution of product was then analysed by HPLC and $^{13}C$ NMR and shown to be composed of a mass fraction of 90% of the tris-substituted products (2,4,6-tris-n-butyl-carbamoyl-1,3,5-triazine, 2,4,6-tris-methyl-carbamoyl-1,3,5-triazine, and mixed 2,4,6-tris-n-butyl-methyl-carbamoyl-1,3,5-triazines) with a mass fraction of 10% of the bis-substituted products (bis-n-butyl-carbamoyl-1,3,5-triazine, bis-n-methyl-carbamoyl-1,3,5-triazine, and mixed n-butyl-methyl-carbamoyl-1,3,5-triazine) including traces of mono-n-butyl-carbamoyl-1,3,5-triazine and mono-methylcarbamoyl-1,3,5-triazine. The mass recovery of the product was 94% of the calculated value.

EXAMPLE 10

To a 1 L four necked resin kettle ("reactor 1"), equipped with a dry-ice condenser, an equal pressure addition funnel, an overhead mechanical stirrer attached to a stainless steel stirring shaft containing one pitched blade and ending in a U-anchor blade, a heating mantle and an inlet for a dry nitrogen were added over an hour with stirring in the following order: 207 g of a solution of sodium n-butoxide in n-butanol having a mass fraction of solids of 21%, 50 g of anhydrous n-butanol, 28 g of tert.-butanol, 2.4 g of sodium tert.-butoxide, 15 g of melamine and 34.5 g of dimethylcarbonate with a dry nitrogen sparge. The total mass fraction of the reaction solids after all reagent additions was approximately 16%. Under continued stirring the resulting white slurry was then heated to 90° C. The light viscous slurry was held at 90° C. for seventy minutes and the reaction mixture was then cooled to 64° C. To a second reactor ("reactor 2"), with good stirring, 34 g of glacial acetic acid (mass fraction of $CH_3COOH$ of 99%) were slowly added to 49 g of n-butanol at 18° C. After complete addition of the glacial acetic acid to the n-butanol in reactor 2, the acidic butanol solution was then transferred slowly in portions to reactor 1 under good stirring and cooling, keeping the temperature in reactor 1 between 60° C. and 64° C. during the addition. After addition of butanolic acetic acid was complete, the final pH of the reaction mixture (measured as supra on a dilution of 3 g of reaction mixture sample in 3 g of water) was adjusted to a pH value between 4.5 and 6.5, if necessary, with further solution of acetic acid in n-butanol. The reaction mixture was then washed with several portions of water and the organic solvent layer containing the product was then analysed by HPLC and $^{13}C$ NMR and shown to be composed of mass fractions of approximately 90% of the tris-substituted products (2,4,6-tris-n-butyl-carbamoyl-1,3,5-triazine, 2,4,6-tris-methyl-carbamoyl-1,3,5-triazine, and mixed 2,4,6-tris-n-butyl-methylcarbamoyl-1,3,5-triazines), with approximately 10% of the bis-substituted products (bis-n-butyl-carbamoyl-1,3,5-triazine, bis-n-methyl-carbamoyl-1,3,5-triazine, and mixed n-butyl-methyl-carbamoyl-1,3,5-triazine) including traces of mono-n-butyl-carbamoyl-1,3,5-triazine and mono-methylcarbamoyl-1,3,5-triazine.

The following table 1 lists the key parameters of the experiments:

TABLE 1

| Example | Unit | Comp. ex. 1 | Comp. ex. 2 | 2 | 3 | 4 | 5 | 6 | 7 | 8 | 9 | 10 |
|---|---|---|---|---|---|---|---|---|---|---|---|---|
| $NaOR^1$ $R^1=$ | | n-Bu | n-Bu | n-Bu | n-Bu + tBu | tert.-Bu | tert.-Bu | tert.-amyl | tert.-Bu | n-Bu | n-Bu | n-Bu |
| $NaOR^0$ $R^0=$ | | — | — | — | — | — | — | — | — | tert.-Bu | tert.-Bu | tert.-Bu |
| m(NaOR) | g | 50.4 | 50.4 | 50.4 | 85.14 | 76 | 96.0 | 73.5 | 76 | 43.47 + 2.4 | 47.67 + 3 | 43.47 + 2.4 |

TABLE 1-continued

| Example | Unit | Comp. ex. 1 | Comp. ex. 2 | 2 | 3 | 4 | 5 | 6 | 7 | 8 | 9 | 10 |
|---|---|---|---|---|---|---|---|---|---|---|---|---|
| m(Mel) | g | 15.8 | 15.8 | 15.8 | 26.9 | 25 | 31.5 | 20 | 25 | 15 | 16 | 15 |
| m(ROH) | g | 189.6 | 189.6 | 189.6 | 387.9 | 600 | 444 | 555 | 400 | 233.53 + 27.5 | 179.33 + 30 | 213.53 + 28 |
| NaOR concentration as multiple of standard | | 1.0 x | 1.0 x | 1.0 x | 1.3 x | 1.0 x | 1.5 x | 1.0 x | 1.6 x | 1.0 x | 1.2 x | 1.0 x |
| w(n-BuOH) | % | 100 | 100 | 84 | 86 | 100 | 100 | 100 | 83 | 90 | 86 | 89 |
| w (tert.-BuOH) | % | 0 | 0 | 16 * | 14 | 0 | 0 | 0 | 0 | 10 | 14 | 11 |
| w (Xylenes) | % | 0 | 0 | 0 | 0 | 0 | 0 | 0 | 17 | 0 | 0 | 0 |
| $\eta$ at 90° C. | Pa · s | 340 | 340 | 39 | 9 | 7 | 300 | 33 | 36 | 32 | 111 | 32 |
| T ($\eta$ > 500 Pa · s) | ° C. | 80 | 80 | 43 | 17 | 21 | 69 | 28 | <20 | 32 | 48 | |
| mass fraction of lower substituted products | cg/g = % | 3 | 16 | | 6 | 10 | 10 | 4 | 7 | 7 | 10 | 10 |
| Neutr.Temp. | ° C. | 17.5 | 65 | 27.5 | 30 | 22.5 | 17 | 31.5 | 37.5 | 36 | 36 | 62 |

R: alkyl group in the sodium alkoxide
m: mass of component
w: mass fraction of component (n-butanol, tert.-butanol, xylene isomer mixture) in the solvent
* added after the reaction
$\eta$: dynamic viscosity
T ($\eta$ > 500 Pa · s): temperature where the viscosity rises to more than 500 Pa · s upon cooling from reaction temperature
lower substituted products include 2,4-bis-(alkoxycarbamoyl)-6-amino-1,3,5-triazine and 2-alkoxycarbamoyl-4,6-diamino-1,3,5-triazine
Neutr. Temp: neutralisation temperature (when adding the acid)

It can be seen from this table that use of a solvent where the alcohol (n-butanol) is derived from the same alkyl radical as is the alkoxide used (sodium n-butoxide, comparative example 1), leads to very high viscosity of the reaction mixture measured at 90° C. after completion of the reaction. Admixture of tert.-butanol to the n-butanol used as solvent, together with sodium butoxide, lowers the viscosity of the reaction mixture after reaction, and more marked if the secondary solvent is added before the reaction (example 3) than in the case when the secondary solvent is added after the reaction (example 2). A slightly higher mass fraction of tert.-butanol in the solvent mixture allows to increase the amount of sodium butoxide by 30 without increase of viscosity. In other words, a higher concentration can be used when increasing the amount of secondary solvent component. This leads, in the technical practice, to an increase in space-time yield which is important for the economics of a chemical reaction. Use of sodium tert.-butoxide in n-butanol as solvent has about the same effect as addition of tert.-butanol as secondary solvent component to the primary solvent component, n-butanol, see example 4 in comparison to example 2. Addition of a secondary solvent component combined with the use of different alkyl groups in the alkanol solvent component and the alkali alkoxide (example 7) shows a synergy between these two measures, even at more increased alkali alkoxide concentration, and is therefore the most preferred embodiment. A similar effect as in example 7 with xylene can be shown when using ketone, ether or other hydrocarbon solvents such as methyl isobutyl ketone, diethylene glycol dibutylether, tetralin and decalin.

The invention claimed is:
1. A process for the preparation of one or more triazine carbamates comprising reacting a mixture of
an aminotriazine A having at least two amino groups per molecule,
an organic carbonate C, and
a base B which is an alkoxide $M(OR^1)_a$ of a metal M which is selected from the group consisting of alkali metals (a =1) and earth alkali metals (a =2), or mixtures thereof with a further alkoxide)$M(OR^0)_a$, where $R^0$ and $R^1$ are different from each other,
in the presence of a solvent S,
wherein the solvent S is
a monohydric alcohol solvent $R^2OH$, or
a mixture of solvents that comprises a mass fraction of at least 10% of a monohydric alcohol $R^2OH$, and a monohydric alcohol solvent $R^3OH$, where $R^2$ and $R^3$ are different from each other, or
a mixture of solvents that comprises a mass fraction of at least 10% of a monohydric alcohol $R^2OH$ with a further solvent selected from the group consisting of multifunctional alcohols having two or more hydroxyl groups per molecule, and from two to twelve carbon atoms, ether, and hydrocarbon solvents, or
a mixture of solvents that comprises a mass fraction of at least 10% of a monohydric alcohol $R^3OH$ with a further solvent selected from the group consisting of ether and hydrocarbon solvents,
wherein $R^0$ and $R^1$ and $R^2$ and $R^3$ are each independently selected from the group consisting of alkyl groups having from one to twenty carbon atoms and each are linear, branched or cyclic,
wherein at least one of the alkyl groups $R^1$ and $R^2$ if present, and $R^3$ if present, and $R^0$ if present, is a tertiary alkyl group, and
wherein there is at least one alkyl group $R^i$ selected from the group consisting of $R^0$, $R^1$, $R^2$, and $R^3$ wherein i is one of 0, 1, 2, and 3, for which the following relations are true:
$R^i \neq R^j$ for all j selected from the group consisting of 0, 1, 2, and 3 with the condition that i≠j, and
$n(R^i) \leq [n(R^0)+n(R^1)+n(R^2)+n(R^3)] \cdot 0.02$,
where n(R) is the amount of substance, with the SI unit "mol", of an alkyl group R which stands for any of $R^0$, $R^1$, $R^2$, and $R^3$.

2. The process of claim 1 wherein $R^1$ is a tertiary alkyl group.

3. The process of claim 1 wherein $R^3$ is a tertiary alkyl group.

4. The process of claim 1 wherein $R^1$ and $R^3$ are tertiary alkyl groups.

5. The process of claim 1 wherein the aminotriazine A has at least two primary amino groups, and is selected from the group consisting of melamine, formoguanamine, acetoguanamine, benzoguanamine and caprinoguanamine, an N-alkylmelamine, and an N,N-dialkylmelamine, wherein, in the N-alkylmelamine and the N,N-dialkylmelamine, the alkyl groups are the same or are different, and the alkyl groups individually have from one to twenty carbon atoms, and are linear or branched, if the number of carbon atoms is three or more, or cyclic, if the number of carbon atoms is three or more.

6. The process of claim 1 wherein the base comprises metal alkoxides which are prepared in situ from corresponding metals or metal compounds by heating a mixture of a metal, or a metal compound, with an alcohol having from one to twenty carbon atoms, optionally in the presence of an entrainment agent, wherein the metal compounds are individually selected from the group consisting of metal hydrides, metal oxides, metal hydroxides, metal amides, metal alkoxides, and organometal compounds.

7. The process of claim 1 wherein the organic carbonate C has the structure $R^4O$—CO—$OR^5$, where $R^4$ and $R^5$ are the same or are different, and are individually selecteld from the group consisting of alkyl radicals having from one to twenty carbon atoms, and are linear or branched if the number of carbon atoms is three or more, or cyclic if the number of carbon atoms is three or more, or are together form an alkane diyl radical having from two to twenty carbon atoms, and are linear or branched, if the number of carbon atoms is three or more, or cyclic, if the number of carbon atoms is three or more.

8. The process of claim 1 wherein the aminotriazine A is selected from the group consisting of melamine, acetoguanamine, and benzoguanamine.

9. The process of claim 1 which comprises after reaction of the mixture of
an aminotriazine A having at least two amino groups per molecule,
an organic carbonate C, and
a base B selected from the group consisting of alkoxides of metals M in the solvent S,
an additional step of adding, to the products of the said reaction, an acid or a solution of an acid in a solvent S' which is the same as the solvent S or is different therefrom, or adding the products of the reaction to an acid or a solution of an acid in a solvent S' which is the same as the solvent S or is different therefrom.

10. The process of claim 1 where the base is a tert-butoxide of an alkali metal.

11. The process of claim 10 where the alkali metal is selected from the group consisting of lithium, sodium and potassium.

12. The process of claim 1 where the base is a mixture of n-butoxides and tert-butoxides of an alkali metal.

13. The process of claim 1 wherein the solvent S comprises n-butanol.

14. The process of claim 13 where the solvent S additionally comprises tert-butanol.

15. The process of claim 13 where the solvent S additionally comprises xylene.

16. The process of claim 9 where the acid is selected from the group consisting of nitric acid, sulphuric acid, phosphoric acid, formic acid, and acetic acid.

17. The process of claim 9 wherein the acid dissolved in a solvent S' is selected from the group consisting of n-butanol, tert-butanol, and water.

18. The process of claim 1 wherein $R^2$ or $R^3$ is a tertiary alkyl group.

* * * * *